(12) United States Patent
Kang et al.

(10) Patent No.: US 11,851,641 B2
(45) Date of Patent: Dec. 26, 2023

(54) METHOD FOR PRODUCING STEM CELL CULTURE PLATE AVAILABLE FOR TISSUE ENGINEERING USING 3D PRINTING FOR HUMAN ORGANOID GENERATION

(71) Applicants: HAN BIO USA, Los Angeles, CA (US); HANBIO CO., LTD., Seoul (KR)

(72) Inventors: Dawitt Kang, Seoul (KR); Hyunchul Kang, Bucheon-si (KR); Jungin Yoon, Hwaseong-si (KR); Chaeyeon Kim, Jeollanam-do (KR); Jeongwon Rho, Seoul (KR)

(73) Assignees: HAN BIO USA; HANBIO CO., LTD., Seoul (KR)

( * ) Notice: Subject to any disclaimer, the term of this patent is extended or adjusted under 35 U.S.C. 154(b) by 444 days.

(21) Appl. No.: 16/923,868

(22) Filed: Jul. 8, 2020

(65) Prior Publication Data

US 2021/0062125 A1   Mar. 4, 2021

Related U.S. Application Data

(60) Provisional application No. 62/894,483, filed on Aug. 30, 2019.

(51) Int. Cl.
| | |
|---|---|
| *B33Y 10/00* | (2015.01) |
| *C12M 3/00* | (2006.01) |
| *C12N 5/077* | (2010.01) |
| *B33Y 80/00* | (2015.01) |
| *B29C 64/118* | (2017.01) |

(Continued)

(52) U.S. Cl.
CPC ........... *C12M 21/08* (2013.01); *B29C 64/118* (2017.08); *B33Y 10/00* (2014.12); *B33Y 70/00* (2014.12); *B33Y 80/00* (2014.12); *C12N 5/0653* (2013.01); *C12N 5/0654* (2013.01); *C12N 5/0658* (2013.01); *B29K 2067/046* (2013.01);

(Continued)

(58) Field of Classification Search
None
See application file for complete search history.

(56) References Cited

U.S. PATENT DOCUMENTS

| | | | | |
|---|---|---|---|---|
| 5,490,962 A | * | 2/1996 | Cima | ...................... A61L 27/60 |
| | | | | 264/41 |
| 2014/0199276 A1* | | 7/2014 | Xu | ....................... D01D 5/0007 |
| | | | | 427/2.24 |

(Continued)

*Primary Examiner* — Mohammad M Ameen
(74) *Attorney, Agent, or Firm* — NKL LAW; Jae Youn Kim (57) ABSTRACT

A method for producing a cell culture plate for human organoid generation using 3D printing is proposed. The method includes the steps of: (a) feeding filament-shaped biodegradable polymer materials, which are not toxic to the human body, and a compatibilizer for improving interfacial adhesion between the polymer materials, into a 3D printer; and (b) producing a cell culture plate using the 3D printer. The cell culture plate is produced by feeding biodegradable polymer materials, which is a blended combination of PLA and PCL, and an appropriate compatibilizer, into a 3D printer. The produced cell culture plate is not toxic to the human body, can culture cells in a desired shape, and has excellent biocompatibility so that it can be applied directly in vivo without detaching cells from the plate.

3 Claims, 9 Drawing Sheets
(9 of 9 Drawing Sheet(s) Filed in Color)

(51) Int. Cl.
   *B33Y 70/00*      (2020.01)
   *B29K 67/00*      (2006.01)

(52) U.S. Cl.
   CPC .................. *B29K 2995/006* (2013.01); *C12N 2506/1384* (2013.01); *C12N 2513/00* (2013.01)

(56) References Cited

U.S. PATENT DOCUMENTS

| | | | |
|---|---|---|---|
| 2015/0224226 A1* | 8/2015 | Bhatia | A61L 27/38 435/174 |
| 2018/0055643 A1* | 3/2018 | Castro | C08J 9/26 |
| 2020/0040183 A1* | 2/2020 | Krishnaswamy | C08L 77/06 |
| 2022/0177697 A1* | 6/2022 | Guillamot | C09D 167/02 |

* cited by examiner

METHOD FOR PRODUCING STEM CELL CULTURE PLATE AVAILABLE FOR TISSUE ENGINEERING USING 3D PRINTING FOR HUMAN ORGANOID GENERATION

CROSS-REFERENCE TO RELATED APPLICATION

This application claims priority from and the benefit of U.S. Provisional Application No. 62/894,483 filed on Aug. 30, 2019, which is hereby incorporated by reference for all purposes as if set forth herein.

BACKGROUND OF THE INVENTION

Field of the Invention

The present disclosure relate to a method for producing a cell culture plate for human organoid generation using 3D printing, and more particularly, to a method for producing a biocompatible cell culture plate for human organoid generation, which includes materials suitable for tissue engineering, selected by evaluating the mechanical properties and biocompatibility thereof, may be used to culture cells in a desired shape by 3D printing, and may be applied directly in vivo without detaching cells from the plate.

Background Art

Currently, there are many reports on the clinical application of 3D printing technology for surgical simulation based on medical imaging technology and the production of surgical guide tools, and the 3D printing technology is also used in Korea. However, it is considered that the research and development of replacements for human soft tissue replacements has been activated since the 3D printing technology was introduced to domestic clinical researchers interested in tissue regeneration and artificial organs.

Models that form three-dimensional (3D) structures by stacking inorganic material layers have been studied since the 1980s. Unlike conventional methods of producing products by cutting or chopping materials, 3D printing works by innumerable thin layers one by one, and thus is also referred to as additive manufacturing technology (Klebe R J. Exp Cell Res 1988; 179: 362-73; Derby B. Science 2012; 338: 921-6). 3D printing technology is divided according to the stacking method and the material used. 3D printing technology is divided, according to the stacking method, into extrusion, spraying, photocuring, sintering, drawing, precipitation, bonding, etc. and materials for 3D printing are various, including polymers, metals, paper, wood, food materials, biomaterials, etc. (Seung-Jae Lee. The future of the health industry to be changed by 3D printing technology. Cheongwon: Korea Health Industry Development Institute, 2014; Chang-Hyun Lee. Use and prospect of 3D printers in medical industry. Daejeon: Institute for Information & Communications Technology Promotion, 2014; Suk-Hee Park. Continuous development of biomaterials and expansion of use of 3D printing customized technology. Health Industry Trends 2014; 28:22-7). As 3D printing technology has recently been applied to tissue engineering technology, innovation has been brought into the field of patient-specific tissue regeneration, and new possibilities are been opened. Since the beginning of 2000, 3D printing technology has been used to produce cell scaffolds, and efforts were made to make three-dimensional cell scaffolds using biomaterials capable of adhering to cells or to regenerate target tissues using 3D printers capable of injecting cells into geometric patterns (Xu T, et. al., Biomaterials 2005; 26: 93-9). This type of technology is a 3D printing technology known as bio-printing.

Organ transplant cases reported to date are examples of application to bladder and trachea, and the application of the bio-printing technology to organs with complicated structures is still difficult (Ventola CL. Medical applications for 3D printing: current and projected uses. P T 2014; 39: 704-118). Accordingly, studies on the regeneration of tissues with sub-concepts and simple structures rather than organs have been actively conducted. In particular, studies have been actively conducted on organs with simple structures, such as bone, cartilage, skin, blood vessels, myocardium, cornea, liver, lung, etc. (Orlando G, et. al, Transplantation 2011; 91: 1310-7).

The development of 3D printing technology in the medical device field for the replacement of human tissues can be found in the field of development of blood vessel scaffolds and skin scaffolds that need to be produced in a tailor-made manner according to individuals and anatomical locations. This is because artificial blood vessels that are currently commercialized can be supplied only with a certain dimension (diameter), but the application of the 3D printing technology makes it possible to produce scaffolds in consideration of the blood vessel diameter and the complexity of the anastomosis for each patient. In addition, when conventional non-biodegradable materials are used, re-surgery is required due to vascular stenosis or the like after a certain period of use, or there is difficulty in considering the growth of a child. Hence, studies have been conducted on the development of biodegradable materials that can be applied to the 3D printing technology.

The development of materials applicable to the 3D printing technology is a major factor along with the development of technology for applying the 3D printing technology. PCL (polycaprolactone), PLA (polylactic acid), PDO (polydioxanone), PGA (polyglycolide), PLGA (polyglycolactide), PEG (polyethylene glycol), collagen, etc., which are biodegradable materials, and PU (polyurethane), PET (polyethylene terephthalate), which are non-biodegradable materials, have been studied as materials for human tissue replacement, and whether or not a material is developed into a product can be determined depending on the degradability, degradation rate, printability, strength, flexibility and the like of the material.

In addition, research and development fields for human tissue replacement, the research and development of bio-printing using stem cells and the like has been actively conducted, and thus it is necessary to refer to trends in the field.

Moreover, biodegradable polymers are widely used in the fields of environmental and biomedical engineering due to their excellent mechanical properties and natural degradability. As the number of disposable packaging materials used for food and pharmaceuticals rapidly increases, it is desirable to develop environmentally friendly materials that can be degraded naturally.

Accordingly, the present inventors have made efforts to develop a cell culture plate for human organoid development using 3D printing, and as a result, have found that a cell culture plate produced by feeding biodegradable polymer materials, which are a blended combination of PLA and PCL, and an appropriate compatibilizer, into a 3D printer, is not toxic to the human body, can culture cells in a desired shape, and has excellent biocompatibility so that the plate can be applied directly in vivo without detaching cells from the plate, thereby completing the present disclosure.

SUMMARY OF THE INVENTION

It is an object of the present disclosure to a method for producing a cell culture plate, which may be used for tissue engineering with a 3D printer for producing a human organoid and has excellent biocompatibility.

To achieve the above object, the present disclosure provides a method for producing a cell culture plate for human organoid generation, the method including steps of: (a) feeding filament-shaped biodegradable polymer materials, which are not toxic to the human body, and a compatibilizer for improving the interfacial adhesion between the polymer materials, into a 3D printer; and (b) producing the cell culture plate using the 3D printer.

The present disclosure also provides a cell culture plate produced by the method.

The present disclosure also provides a method for producing a cell complex, the method including a step of culturing cells in the cell culture plate.

The present disclosure also provides a cell complex produced by the method.

Hereinafter, the present disclosure will be described in detail.

The present disclosure provides a method for producing a cell culture plate for human organoid generation, the method including steps of: (a) feeding filament-shaped biodegradable polymer materials, which are not toxic to the human body, and a compatibilizer for improving the interfacial adhesion between the polymer materials, into a 3D printer; and (b) producing the cell culture plate using the 3D printer.

In the method for producing a cell culture plate for human organoid generation according to the present disclosure, the biodegradable polymers are preferably materials selected from the group consisting of PCL (polycaprolactone), PLA (polylactic acid), PDO (polydioxanone), PGA (polyglycolide), PLGA (polyglycolactide), PEG (polyethylene glycol), PHB (polyhydroxybutyrate), PHV (polyhydroxyvalerate), and propylene fumarate, copolymers thereof, and combinations thereof. The biodegradable polymers are more preferably a combination of PLA and PCL. The weight ratio between PLA and PCL is more preferably 99:1 to 9:1, even more preferably 97:1 to 97: 10, most preferably 97:3.

In addition, in the method for producing a cell culture plate for human organoid generation according to the present disclosure, the compatibilizer is preferably a material selected from the group consisting of glycidyl methacrylate (GMA), dicumyl peroxide (DCP), tributyl citrate (TBC), triphenyl phosphate (TPP), and lysine triisocyanate (LTI).

The present disclosure also provides a cell culture plate produced by the method.

In the cell culture plate of the present disclosure, the plate preferably includes cells cultured directly on the plate. The cells are preferably stem cells or cells that differentiated from stem cells. More preferably, the cells are cells selected from the group consisting of adipose-derived mesenchymal stem cells, adipocytes, myocytes, osteocytes, vascular cells, corneal cells, dentin, and hepatocytes, pancreatic cells, nerve tissue cells, skeletal muscle cells, and skin cells. Even more preferably, the cells are cells selected from the group consisting of adipocytes, myocytes, and osteocytes.

In addition, in the cell culture plate of the present disclosure, the cell culture plate is preferably tailored to the shape of a damaged defective part. Preferably, the cell culture plate is preferably introduced into a subject without detaching cells from the plate. Preferably, the cell culture plate is a multilayer plate in which the cell culture plate is stacked in two or more layers.

The present disclosure also provides a method for producing a cell complex, the method including a step of culturing cells in the cell culture plate.

In the method for producing a cell complex according to the present disclosure, the cells are preferably stem cells or cells that differentiated from stem cells. The stem cells are preferably adipose stem cells. More preferably, the cells are cells selected from the group consisting of adipose-derived mesenchymal stem cells, adipocytes, myocytes, osteocytes, vascular cells, corneal cells, dentin, and hepatocytes, pancreatic cells, nerve tissue cells, skeletal muscle cells, and skin cells. Even more preferably, the cells are cells selected from the group consisting of adipocytes, myocytes, and osteocytes. In addition, the cell culture plate is stacked in two or more layers.

The present disclosure also provides a cell complex produced by the method.

In the cell complex of the present disclosure, the cell complex is preferably applicable to the human body without additional detachment and a process of loading onto a scaffold.

Biodegradable polymers are not only environmentally friendly materials, but also have excellent biocompatibility, and thus can be used as scaffolds that may be transplanted in vivo. For example, sutures should be able to temporarily function as scaffolds, and should ensure rapid cell growth and repair. In addition, sutures should be strong enough to hold tissue tightly after suturing, and at the same time, should be flexible enough to be knotted. Therefore, biodegradable polymers having high strength, low modulus and proper elongation are used.

Poly(lactic acid) (PLA) that is used in the present disclosure is a biodegradable aliphatic polyester that can be obtained from renewable resources, and can be extracted by fermentation of polysaccharides. PLA is highly brittle, and the use thereof in various fields is limited due to its low heat resistance and limited gas bather properties. On the other hand, poly(e-caprolactone) (PCL) has high impact strength, but the yield strength and elastic modulus thereof are very low.

To improve the brittle property of PLA, a lot of studies have been conducted on a method of blending the flexible polymer PCL. PLA and PCL are immiscible so that phase separation therebetween easily occurs, and the two separated phases have poor interfacial adhesion. Hence, a blend of PLA/PCL cannot be combined in thermodynamic terms. When the formation of an interface between the two materials occurs, the physical properties of the materials become weakened. For this reason, in the present disclosure, a compatibilizer is added.

Addition of compatibilizers having small molecular weights, such as glycidyl methacrylate (GMA), dicumyl peroxide (DCP), tributyl citrate (TBC), tripheny phosphite (TPP) and lysine triisocyanate (LTI), reduces the size of dispersed phases and increases the strength of PLA. Thus, even a small amount of the compatibilizer increases the elongation of PLA/PCL and the impact strength is increased by causing a crosslinking reaction. Compatibilizers, such as glycidyl methacrylate (GMA), dicumyl peroxide (DCP), and lysine triisocyanate (LTI), are difficult to produce or are highly toxic, and hence addition of these compatibilizers is unsuitable in terms of environmental friendliness.

Although many studies have been conducted to increase the mechanical properties of PLA/PCL films, these studies have focused mainly on mechanical properties and synthesis, and hence the range thereof is limited to environmentally friendly packaging materials.

BRIEF DESCRIPTION OF THE DRAWINGS

The patent or application file contains at least one drawing/photograph executed in color. Copies of this patent or patent application with color drawing(s)/photograph(s) will be provided by the Office upon request and payment of the necessary fee

In FIG. 4, CPDL denotes cumulative population doubling level.

DETAILED DESCRIPTION OF THE PREFERRED EMBODIMENTS

Hereinafter, the present disclosure will be described in more detail with reference to preferred examples. However, the following examples are provided so that this disclosure will fully convey the scope of the present disclosure to those skilled in the art, and these examples may be modified into various different forms. In addition, the scope of the present disclosure is not limited by these examples.

<Example 1> PLA/PCL Stirring Method

Before an experiment, PLA and PCL were sufficiently dried in vacuum ovens at 95° C. for 12 hours and at 50° C. for 12 hours, respectively. The dried PLA and PCL were added to dichloromethane (DCM) at predetermined ratios and stirred at 300 rpm for 3 hours at room temperature. At this time, each mixture of PLA and PCL was dissolved in a volume equal to 1/10 of DCM. As a compatibilizer, TBC was used and added in an amount equal to 3% of the weight of PCL. The components of each mixture and the contents thereof are shown in Table 1 below.

TABLE 1

|  | PLA | PCL | DMC | TBC (µL) |
| --- | --- | --- | --- | --- |
| 99:1 | 1.97 | 0.02 | 15 ml | 0.58 |
| 97:3 | 1.93 | 0.06 |  | 1.73 |
| 95:5 | 1.89 | 0.1 |  | 2.88 |
| 93:7 | 1.85 | 0.14 |  | 4.03 |

<Example 2> Fabrication of PLA/PCL Films

Films were fabricated using a Teflon mold having a size of 80×9×60 mm$^2$. The fabricated films were dried at room temperature for 24 hours, and then stored in a vacuum oven for 24 hours. The films were fabricated to have a thickness of 0.2 to 0.5 mm.

<Example 3> Comparison of Mechanical Properties Between PLA/PCL Compositions

A tensile strength test was performed using Instron 5564. The test was performed at a speed of 50 mm/min with a force of 2000 N at a room temperature. Test samples were prepared in accordance with ASTM D-638 (type V), and the thicknesses of the samples were measured using a dial gauge.

Figure 1A:
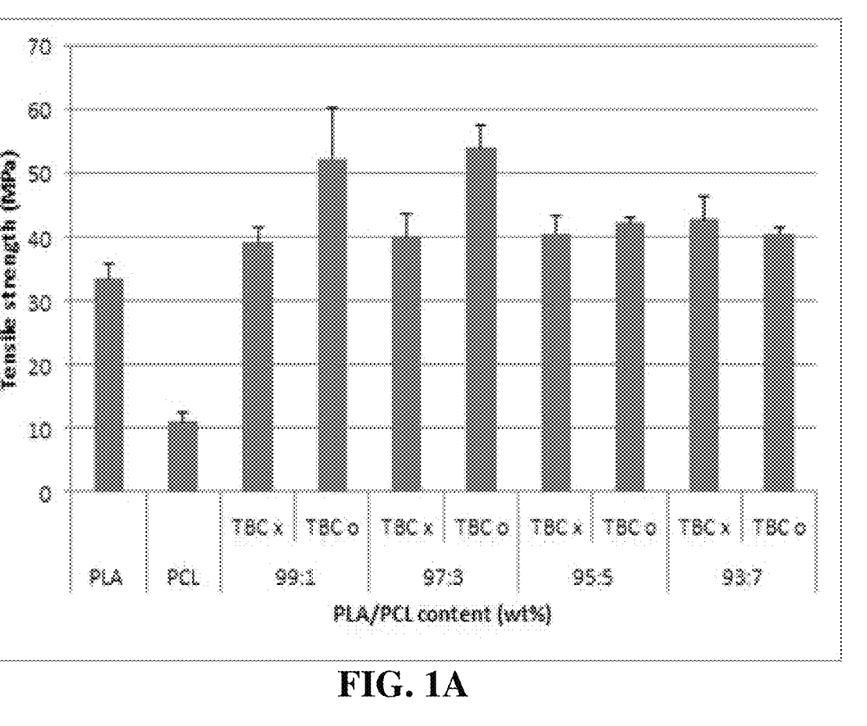
FIGS. 1A and 1B are graphs showing the results of comparing mechanical properties between various PLA/PCL compositions.
Figure 1B:
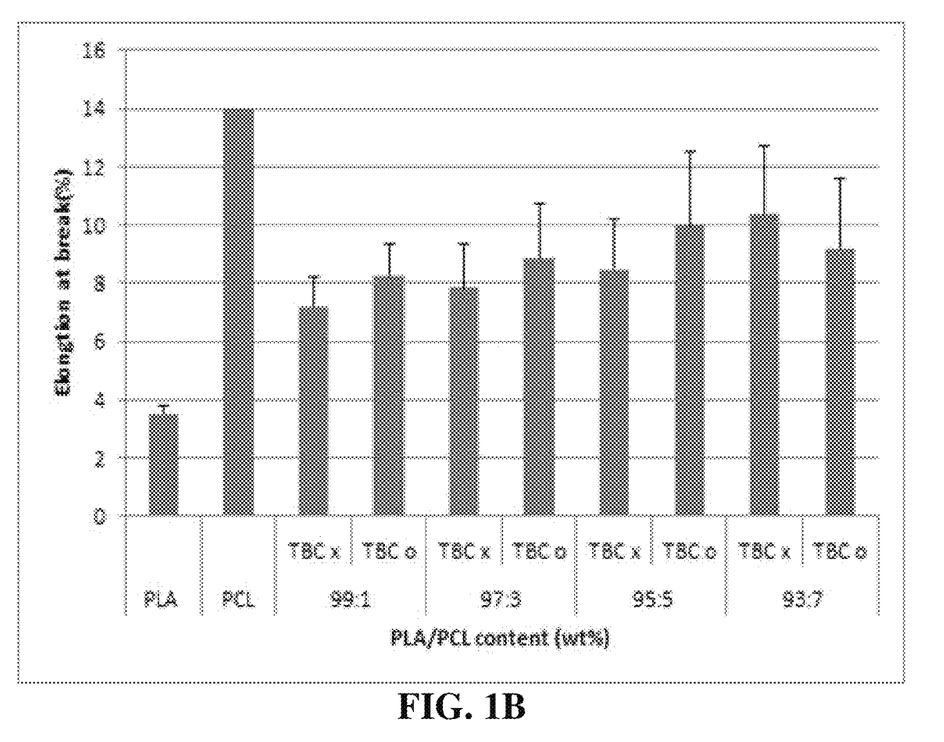

FIGS. 1A and 1B show the results of comparing mechanical properties between the PLA/PCL compositions. 10 wt % PLA had a tensile strength of 33.4±2.5 MPa and an elongation of 3.5±0.5%, and 10 wt % PCL had a tensile strength of 11±1.3 MPa and an elongation of 780±180%. As the content of PCL in each of the PLA/PCL films, to which TBC was not added, increased from 1 to 7%, the tensile strength of the PLA/PCL film slightly increased from 39.2±2.3 to 42.9±3.5 MPa, and the elongation thereof slightly increased from 7.2±1.0 to 10.3±2.3%. Among the PLA/PCL films to which TBC was not added, the condition of 93/7 showed the highest tensile strength and elongation. Combination of PCL with PLA showed the effect of promoting the elasticity of PLA by increasing the bonding force between the molecular chains (identifiable through DMA). However, addition of TBC showed other results. As the content of PCL increased from 1 to 3%, the tensile strength increased from 52.5±7.8 to 54.1±3.4 MPa, but as the content of PCL increased, the tensile strength started to decrease rapidly.

The elongations of the PLA/PCL films seem to be independent of the addition or non-addition of TBC, and are slightly different from each other, but are all within the error range. As the content of PCL in the PLA/PCL film containing TBC increased to 5%, the ductility of the film increased, but the storage modulus (G') of the film decreased, and thus the increased content of PCL resulted in a decrease in the tensile strength.

In the present disclosure, the 97/3 PLA/PCL film containing TBC, which has appropriate ductility and tensile strength compared to untreated PLA/PCL films, was selected as an optimum material than PLA and PCL which were not treated.

Biomaterials must be harmless to the body and are used in close contact with the body. Thus, the biomaterials should essentially have excellent biocompatibility, and the intended uses and applications thereof vary depending on the mechanical/physical properties and molding processability thereof. The biomaterials include polymers, metals, ceramic materials, etc., which are used to replace damaged or dysfunctional human tissues and organs. Metal materials or ceramic materials are frequently used as substitute materials for parts such as bones and teeth, which are hard tissues, and ceramics are used for parts that are not subjected to a high mechanical load, among hard tissues. In addition, polymers are used for relatively soft parts. In particular, there are materials for biological hard tissue, synthetic polymer materials that are used for artificial hearts, artificial blood vessels, dialysis membranes, plasma separation membranes, etc., and biopolymer materials that are used to treat biological tissues.

Regarding the clinical application of biomaterials that are currently commercially available, artificial blood vessels require 150 KPa to withstand a blood pressure of 20 KPa, and artificial valves must withstand a maximum blood pressure of 300 mmHg. In addition, the suitable tensile strength of ophthalmic materials is 0.24 MPa. The PLA/PCL scaffold produced in the present disclosure has a maximum tensile strength of 54.1±3.4 MPa, and may be produced according to the intended use application thereof by changing the composition ratio between PLA and PCL.

<Example 4> Cytotoxicity Test

Cytotoxicity was evaluated based on the standards recommended by the International Organization for Standardization (ISO-10993-5). The standards are shown in Table 2 below. 1X DMEM (Dulbecco's Modified Eagle's Medium (Gibco)) supplemented with 10% FBS (fetal bovine serum (Gibco)) and 1% PS (penicillin-streptomycin) was used, and extraction was performed based on 1.25 $cm^2$ of the PLA/PCL film per mL. Mouse fibroblast L-929 cells were used and cultured in a $CO_2$ incubator for 24 hours. 100 μL of each of the PLA/PCL film, a positive control and a negative control was dispensed into three wells, and the cells were cultured in an incubator for 48 hours. The cultured cells were stained with EZ-cytox, and then quantitatively counted a spectrophotometer (iMark, Bio-Rad, USA) at a wavelength 415 nm.

Through the cytotoxicity test, how the PLA/PCL film affects living cells was examined. As a result of the test, cytotoxicity was not found regardless of whether TBC was added, and even when the number of the cells was measured through quantitative evaluation, the cells showed cell viabilities of 111, 109, 109, 111, 115, 112, 112, 106, and 125%. Since the cell viability exceeded 100%, it was determined that the PLA/PCL film had excellent biocompatibility. In addition, it can be considered that the PLA/PCL film is clinically safe and effective.

TABLE 2

| Thickness (mm) | Elution rate (surface area or mass/ volume) ± 10% | Examples of forms of test materials |
|---|---|---|
| <0.5 | 6 $cm^2$/ml | Thin film, sheet, tubing wall |
| 0.5 to 1.0 | 3 $cm^2$/ml | Tubing wall, slab, small molded items |
| >1.0 | 3 $cm^2$/ml | Larger molded items |
| >1.0 | 1.25 $cm^2$/ml | Elastomeric closures |
| Irregularly shaped solid medical devices | 0.2 g sample/ml | Powder, pellets, foam, non-absorbent molded items |
| Irregularly shaped porous medical devices (low-density materials) | 0.1 g/ml | Membranes |

ISO 10993-12 extraction ratio

<Example 5> Cell Proliferation Assay

For cell proliferation assay, the number of cells over time can be quantitatively evaluated, and observation of the number of cell divisions, metabolic activity, or DNA synthesis can be performed. A cell counting kit-8 (CCK-8, Dojindo Molecular Technologies, Inc., Japan) was used, and as a medium for cell culture, 1×DMEM (Dulbecco's Modified Eagle's Medium (Gibco)) supplemented with 10% FBS (fetal bovine serum (Gibco)) and 1% PS (penicillin-streptomycin) was used. 100 μL of an L929 cell suspension was seeded into a 96-well plate at a density of ($5 \times 10^3$ cells/well), and then cultured in an incubator for 24 hours. Thereafter, 10 μL of the extract at a ratio of 1.25 $cm^2$/mL according to ISO 10993-12 (Table 1) was added to the 96-well plate, and observation was performed every 6, 12, 24 and 48 hours. The absorbance of the stained solution was measured at a wavelength of 450 nm.

Figure 2:
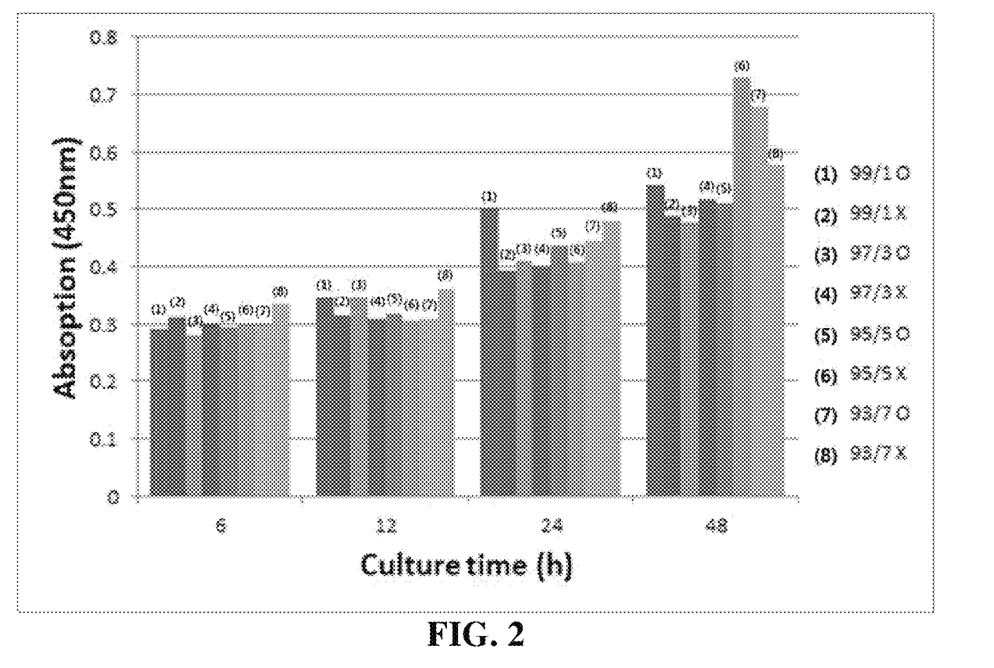
FIG. 2 is a graph showing the results of cell proliferation assay.

FIG. 2 shows the results of the cell proliferation assay. The results of the cell proliferation assay performed using CCK-8 indicated that the L-929 cells well adhered and proliferated. The cells proliferated rapidly after 24 hours, although the proliferation rate was low until 12 hours. Therefore, it was determined that the PLA/PCL film had no cytotoxicity under the conditions of the present disclosure and was clinically safe and effective.

<Example 6> Production of PLA/PCL Plates for Cell Adhesion Using 3D Printing

A filament extruder (FILIBOT) was used to perform 3D printing using the 97/3 PLA/PCL containing no TBC, selected in the previous experiment. Since fillet type material is required to fabricate filaments, PLA/PCL 97/3 was stirred at 300 rpm in dichloromethane (DCM) for 3 hours at room temperature. At this time, the mixture of PLA and PCL was dissolved in a volume equal to 1/10 of DCM, and TBC was added in an amount equal to 3% of the weight of PCL. A film was fabricated using a Teflon mold having a size of 80×9×60 $mm^2$ and dried at room temperature for 24 hours, and then a fillet having a size of 0.5 mm (width)×0.5 mm (length) was fabricated. The fabricated fillet was placed in a filament extruder, the temperature of the extruder was set to 200° C., and the speed of the extruder was set to 4. Filaments for 3D printing were extruded with an optimum thickness of 1.75 mm, and filaments having a thickness of 1 mm were fabricated, which were required to produce PLA/PCL plates. A drawing of a plate having a size of 6.2 mm (width)×6.2 mm (length)×10 mm (height) was prepared using a 3D inventor, and then converted into a file using CURA. Next, plants were produced using 3D printing.

Figure 3:
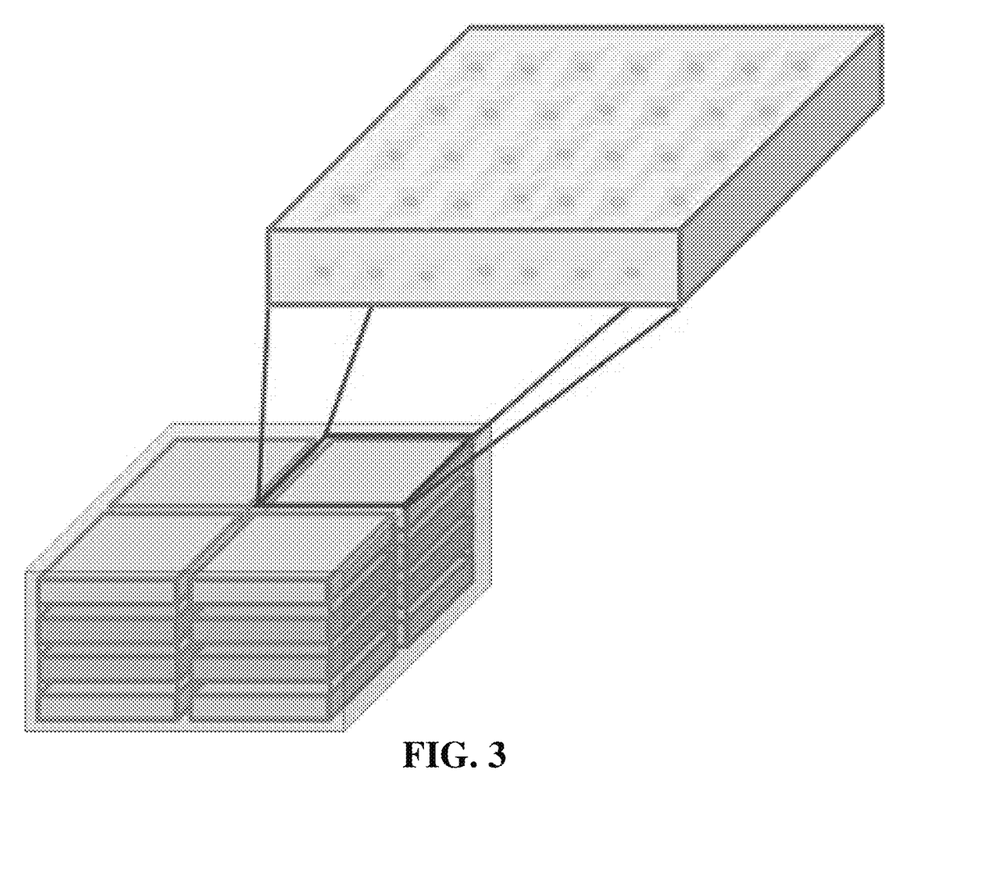
FIG. 3 schematically illustrates plates obtained by placing and stacking four 97/3 PLA/PCL plates containing TBC in each square dish.

As shown in FIG. 3, three 97/3 PLA/PCL plates, each containing TBC, were placed in each square dish.

<Example 7> Experiment on Culture and Differentiation of Cells to be Used in Assay of Cell Adhesion to PLA/PCL Plates <7-1> Culture of Adipose-Derived Mesenchymal Stem Cells from Adipose Tissue Cells to be used in cell adhesion assay were prepared. 50 ml of adipose tissue was obtained by liposuction from the abdominal subcutaneous area, and the obtained adipose tissue was cut finely with sterile scissors. The finely cut adipose tissue was transferred into a 125 ml storage bottle and washed three times with the same amount of PBS (phosphate-buffered saline). An adipose tissue lipolysis reagent was prepared by adding collagenase type 1 for lysing the adipose tissue, 1% fetal bovine serum for ensuring cell stability during lipolysis, and 2% antibiotic for preventing contamination. The collagenase solution was filtered, and then sufficiently warmed to 37° C. before use. The washed adipose tissue was treated with the same volume of the collagenase solution. The bottle containing the collagenase solution and the adipose tissue was placed in a shake incubator and incubated at 37° C. and 130 rpm for 80 minutes, and then the optimum cell yield was confirmed.

The stromal vascular fraction was suspended in stromal medium, inoculated into a culture vessel, and then cultured in an incubator for 24 hours at 37° C. under 5% $CO_2$. As the stromal medium, low-glucose DMEM supplemented with 10% fetal bovine serum and 1% antibiotic was used. After 24 hours, the cell culture was removed and washed with PBS (phosphate-buffered saline). The medium was replaced with fresh stromal medium, and when the cells were grown to a confluency of about 80 to 90%, the cells were passaged.

As the culture medium for passage, low-glucose DMEM supplemented with 10% fetal bovine serum, 1% antibiotic and human basic fibroblast growth factor (FGF) (hereinafter referred to as hbFGF) was used.

Figure 4:
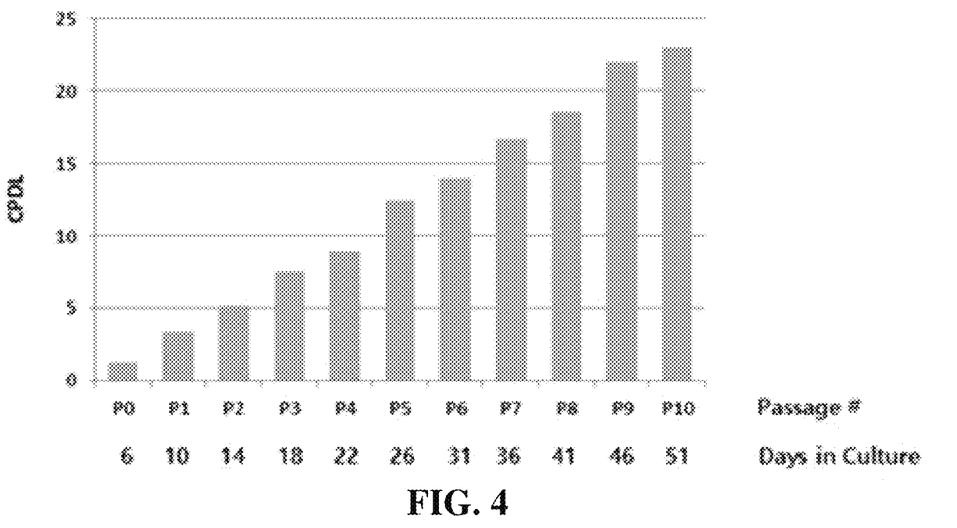
FIG. 4 is a graph showing that adipose stem cells can be proliferated when passaged in vitro.

As a result, the self-renewal of the adipose stem cells was confirmed. As used herein, the term "self-renewal" means the ability of a cell to continuously produce copies of itself through cell proliferation, and adipose stem cells have self-renewal ability. Adipose stem cells have self-renewal ability during in vitro culture, and thus can be produced as pharmaceuticals through the production process. As can be seen in FIG. 4, it was confirmed that, when the adipose stem cells were passaged in vitro, they could proliferate.

<7-2> Experiment on Differentiation of Cultured Adipose-Derived Mesenchymal Stem Cells into Osteocytes, Myocytes and Adipocytes In order to confirm the multipotency of adipose stem cells, an experiment on the induction of differentiation of adipose stem cells was performed under the following conditions or using a commercially available differentiation medium.

Table 3 below shows the compositions of media for inducing differentiation into adipocytes, myocytes and osteocytes, respectively, and Table 4 below shows criteria for measuring the rate of differentiation into each cell type.

TABLE 3

| Differentiation | Compositions of differentiation-inducing media |
| --- | --- |
| Adipocytes | 3% FBS, insulin, dexamethasone, indomethacin, IBMX |
| Myocytes | 10% FBS, 3% horse serum, hydrocortisone |
| Osteocytes | 10% FBS, 1,25-dihydroxyvitamin D3, ascorbic-2-phosphate, b-glycerophosphate |

TABLE 4

| Differentiation | Differentiation rates (criteria for measurement) |
| --- | --- |
| Adipocytes | 95% or more (percentage of cells containing lipid droplets stained with Oil Red O) |
| Myocytes | 90% or more (percentage of myosin-positive cells) |
| Osteocytes | 90% or more (percentage of ALP-positive cells) |

<7-2-1> Differentiation into Adipocytes

Figure 5:
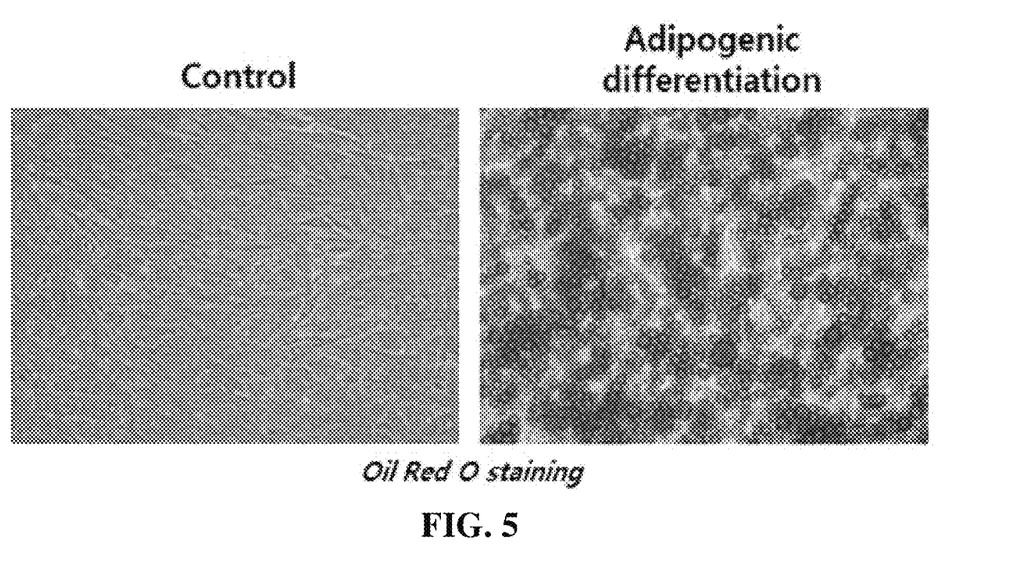
FIG. 5 depicts photographs showing the results of examining the ability of adipose stem cells to differentiate into adipocytes.

In order to confirm the ability of adipose stem cells into adipocytes, adipose stem cells were cultured under conditions for inducing differentiation into adipocytes. After induction of differentiation into adipocytes, lipid droplets accumulated in the cytoplasm of the adipose stem cells in the form of fibroblasts, and the cell morphology changed. It could be confirmed that lipid droplets were stained red with Oil Red O, suggesting that the adipose stem cells differentiated into adipocytes. The results are shown in FIG. 5. Specifically, the adipocyte differentiation-induced group shown in the right photograph in FIG. 5 showed vividly stained distinct lipid droplets compared to the control group (left photograph), suggesting that the adipose stem cells differentiated into adipocytes.

<7-2-2> Differentiation into Myocytes

Figure 6:
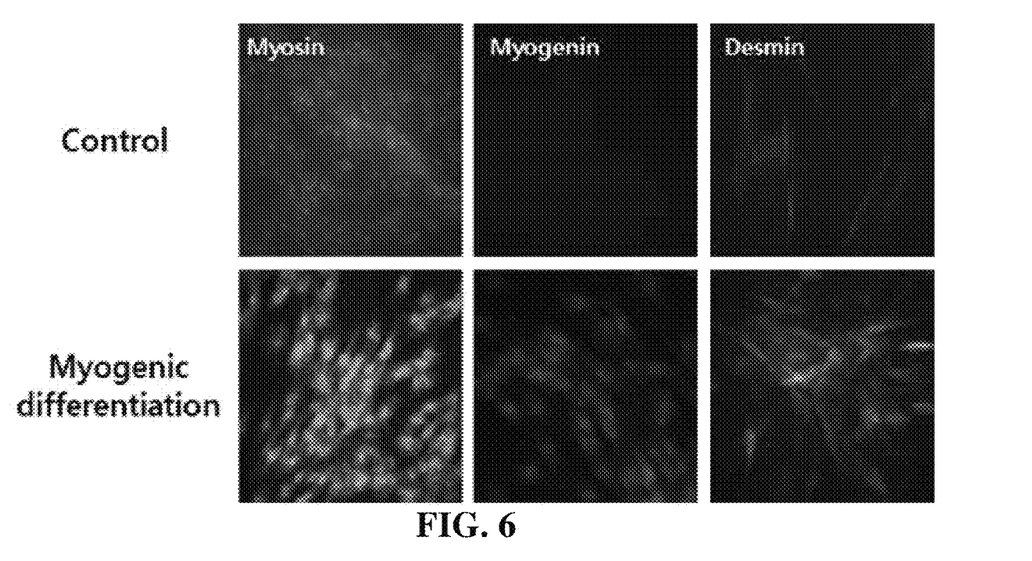
FIG. 6 depicts photographs showing the results of examining the ability of adipose stem cells to differentiate into myocytes.

In order to confirm the ability of adipose stem cells into myocytes, adipose stem cells were treated with a medium for inducing differentiation into myocytes, and differentiation thereof was induced for 2 weeks. Myogenin, desmin, myosin, which are known to be expressed specifically in myocytes, were observed, and the results are shown in FIG. 6. Specifically, it could be confirmed that, in comparison with the control group (upper photograph) in FIG. 6, the group (lower photograph), in which differentiation into myocytes was induced, expressed myogenin, desmin and myosin. This suggests that the adipose stem cells differentiated into myocytes.

<7-2-3> Differentiation into Osteocytes

Figure 7:
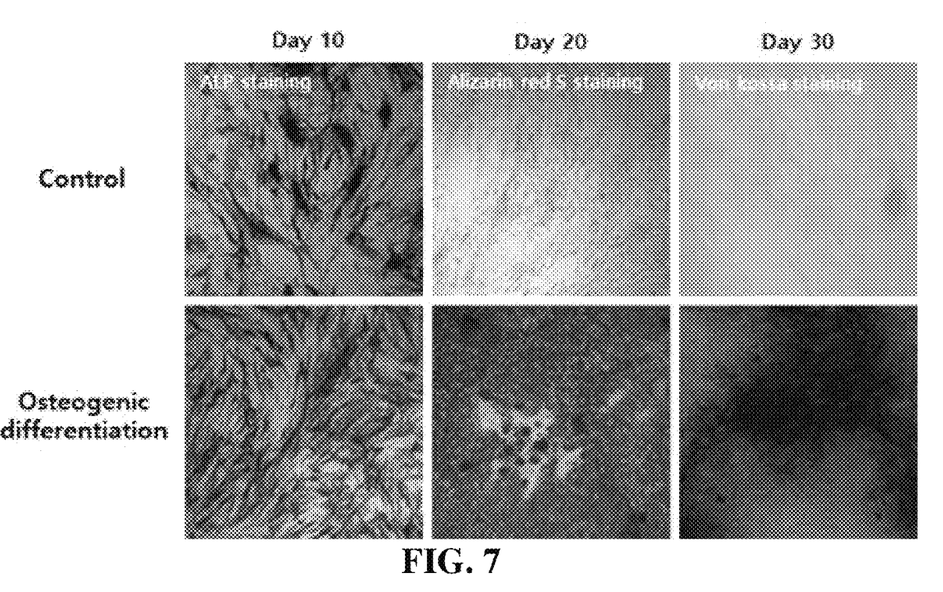
FIG. 7 depicts photographs showing the results of examining the ability of adipose stem cells to differentiate into osteocytes.

In order to confirm the ability of adipose stem cells to differentiate into osteocytes, adipose stem cells were cultured in a medium for inducing differentiation into osteocytes for 30 days. The results are shown in FIG. 7. As can be seen in FIG. 7, it was confirmed that, in comparison with the control group, the differentiation-induced group was stained with the early osteoblast marker ALP on 10 days after differentiation induction (the first photograph at the bottom of FIG. 7), and calcific deposition in the differentiation-induced group was observed by Alizarin red staining on day 20 (the second photograph at the bottom of FIG. 7), and formation of mineralized nodules in the differentiation-induced group was observed by von Kossa staining on day 30 (the third photograph at the bottom of FIG. 7). This suggests that the adipose stem cells differentiated into osteocytes.

<7-3> Assay of Cell Adhesion to PLA/PCL Plates Using Cultured Adipose-Derived Mesenchymal Stem Cells, Osteocytes, Myocytes and Adipocytes Adipose-derived mesenchymal stem cells, osteoblasts, myocytes and adipocytes were seeded into the produced PLA/PCL plates at a density of 3,000 cells/cm$^2$. Each plate was filled with a medium suitable for each cell type, and the cells were cultured for 5 days. Next, the cells that adhered to the PLA/PCL plates were observed under a microscope, and the adhered cells were removed from the bottom by treatment with trypsin EDTA, followed by cell counting.

Each cell type was seeded into the produced PLA/PCL plate at a density of 3,000 cells/cm$^2$, and the adhesion and proliferation rate of the cells were observed for 3 days and 5 days. After 3 days and 5 days of culture, the cells were detached from the culture plates and counted. The results of cell counting are shown in FIG. 8.

Figure 8:
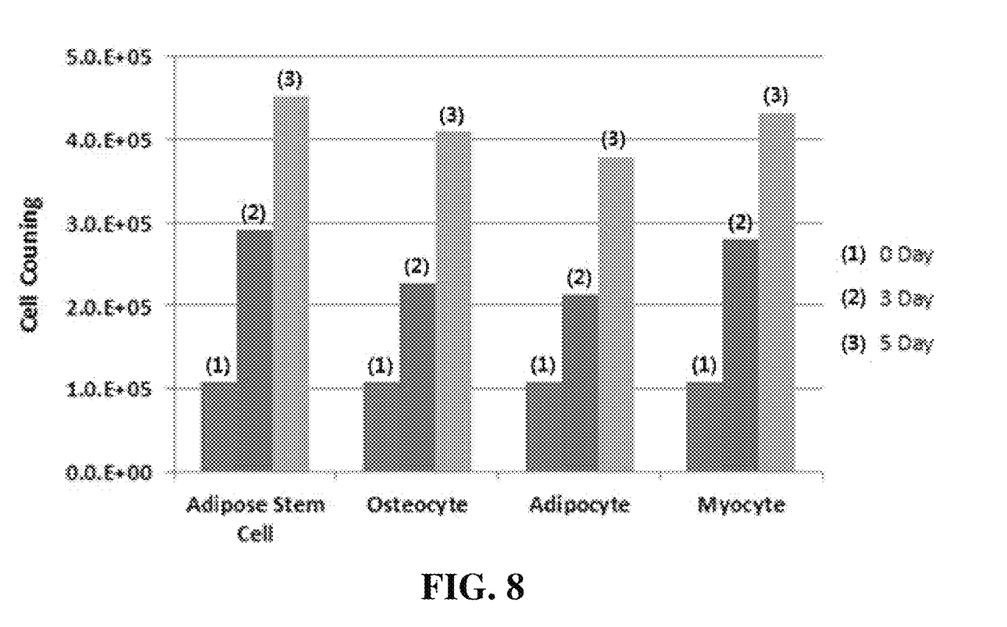
FIG. 8 is a graph showing the results of an assay of cell adhesion to PLA/PCL plates, performed using cultured adipose-derived mesenchymal stem cells, osteocytes, myocytes and adipocytes.

As can be seen in the graph of FIG. 8, it was confirmed that most of the cells showed a proliferation rate of about 2.5-fold on 3 days of culture and a proliferation of about 4-fold on 5 days of culture, indicating that most of the cells adhered.

<Example 8> Biodegradation Assay of PLA_PCL Cell Culture Plate

1) The pH value was adjusted with phosphate buffer solution. The pH value was measured in two different containers in each test, and the pH value was additionally measured in at least two containers every 4 weeks during the entire test period.

2) If the pH value in one container changed beyond the limit, the pH values of all the containers were measured and adjusted to pH 7.4±0.3 using a 0.1 mol/L of NaOH solution.

3) The temperature was maintained at 37±1° C.

4) The sample was completely immersed in buffer solution.

5) Sampling was performed at least five times during a predetermined period of one month or more to one year or less, and the degree of degradation of the sample was measured. At this time, the predetermined period was determined according to the degree of degradation of the raw material.

6) When the predetermined time was reached or the mass loss reached at least 50%, the test was terminated.

7) The degree of degradation can be measured as a change in the molecular weight of the product or as a percentage of mass loss.

8) The mass of the product is expressed as the average of the rates of reduction (initial and subsequent) during the test period.

The cell culture plate for human organoid generation, produced according to the present disclosure configured as described above, is produced by feeding biodegradable polymer materials, which is a blended combination of PLA and PCL, and an appropriate compatibilizer, into a 3D printer. The produced cell culture plate is not toxic to the human body, can culture cells in a desired shape, and has excellent biocompatibility so that it can be applied directly in vivo without detaching cells from the plate.

Although the present disclosure has been described above in detail with reference to preferred embodiments, the present disclosure is not limited by the embodiments, and those skilled in the art will appreciate that various modifications are possible within the scope of the technical idea of the present disclosure.

What is claimed is:

1. A method for producing a cell culture plate for human organoid generation, the method comprising the steps of:
   (a) fabricating a film by dissolving a mixture of polyactic acid (PLA) and polycaprolactone (PCL) in a volume equal to 1/10 of Dichloromethane (DCM) and adding a compatibilizer for improving interfacial adhesion to the mixture in an amount of about 3 wt % of the PCL;
   (b) fabricating a fillet after drying the film at room temperature around 24 hours;
   (c) fabricating a filament of the fillet with a filament extruder; and
   (d) producing the cell culture plate using a 3D printer after feeding the filament into the 3D printer.

2. The method of claim 1, wherein the weight ratio between the PLA and the PCL is 97:3.

3. The method of claim 1, wherein the compatibilizer is a material selected from the group consisting of dicumyl peroxide (DCP), tributyl citrate (TBC), triphenyl phosphate (TPP), and lysine triisocyanate (LTI).

* * * * *